United States Patent
Lin et al.

(10) Patent No.: US 9,540,488 B1
(45) Date of Patent: Jan. 10, 2017

(54) SILOXANE RESIN COMPOSITION, AND PHOTOELECTRIC DEVICE EMPLOYING THE SAME

(71) Applicant: INDUSTRIAL TECHNOLOGY RESEARCH INSTITUTE, Hsinchu (TW)

(72) Inventors: Chih-Hao Lin, Taoyuan (TW); Wen-Bin Chen, Tainan (TW); Ying-Nan Chan, Erlin Township, Changhua County (TW); Shu-Chen Huang, Hsinchu (TW); Kai-Chi Chen, Tsautuen Jen (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/983,938

(22) Filed: Dec. 30, 2015

(30) Foreign Application Priority Data

Dec. 16, 2015 (TW) .............................. 104142226 A

(51) Int. Cl.
C08G 77/14 (2006.01)
H01L 33/56 (2010.01)

(52) U.S. Cl.
CPC .............. *C08G 77/14* (2013.01); *H01L 33/56* (2013.01); *H01L 2933/005* (2013.01); *H01L 2933/0033* (2013.01)

(58) Field of Classification Search
None
See application file for complete search history.

(56) References Cited

U.S. PATENT DOCUMENTS 5,260,349 A 11/1993 Crivello
5,484,950 A * 1/1996 Crivello ................ C07F 7/0852
549/215

(Continued)

FOREIGN PATENT DOCUMENTS

CN 104204100 A 12/2014
TW I325898 B 6/2010
(Continued)

OTHER PUBLICATIONS

Chung et al., "Synthesis of Multifunctional Epoxy Monomers and their Potential Application in the Production of Holographic Photopolymers," J. Ind. Eng. Chem., vol. 12, No. 5, 2006, pp. 783-789.

(Continued)

*Primary Examiner* — Robert S Loewe
(74) *Attorney, Agent, or Firm* — Birch, Stewart, Kolasch & Birch, LLP

(57) ABSTRACT

A siloxane resin and photoelectric device employing the same are provided. The siloxane resin composition includes (a) 45-87 parts by weight of a first siloxane compound represented by Formula (I), wherein each $R^1$ is independently $C_{1-3}$ alkyl group, and n is an integer from 2 to 15;

Formula (I)

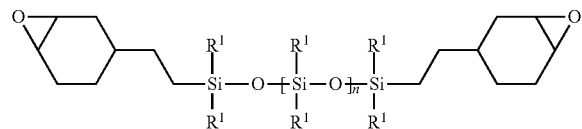

(b) 5-35 parts by weight of a second siloxane compound represented by Formula (II), wherein each $R^2$ and $R^3$ are independently $C_{1-3}$ alkyl group; each $R^4$ is inde-
(Continued)

pendently $C_{1-3}$ alkyl group, or epoxy group; $x \geq 1$, $y \geq 2$, and $x/y$ is from about 0.1 to 3; and

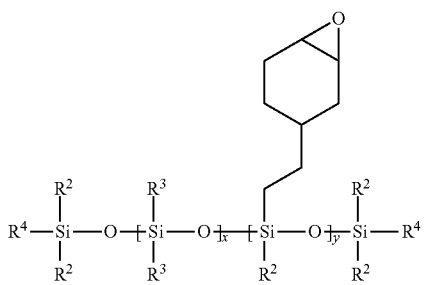

Formula (II)

(c) 2-20 parts by weight of a third siloxane compound represented by Formula (III), wherein each $R^5$ is independently $C_{1-3}$ alkyl group, and the sum of the first siloxane compound, the second siloxane compound, and the third siloxane compound is 100 parts by weight

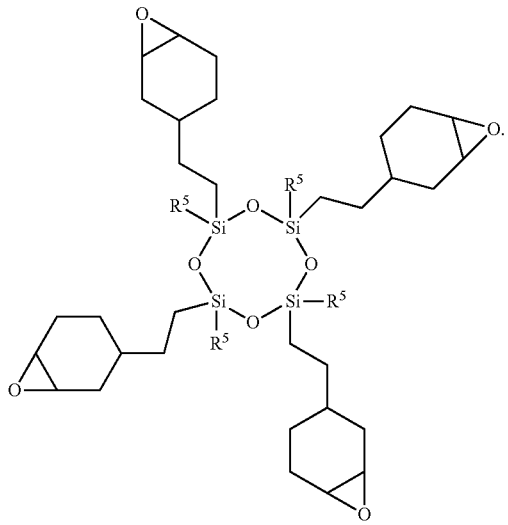

Formula (III)

11 Claims, 1 Drawing Sheet

(56) References Cited

U.S. PATENT DOCUMENTS

| | | | |
|---|---|---|---|
| 5,863,970 A | 1/1999 | Ghoshal et al. | |
| 6,245,828 B1* | 6/2001 | Weinmann | A61K 6/0017 433/228.1 |
| 6,417,243 B1 | 7/2002 | Peeters et al. | |
| 6,779,656 B2* | 8/2004 | Klettke | A61K 6/0017 156/329 |
| 6,806,509 B2 | 10/2004 | Yoshino et al. | |
| 6,962,948 B2* | 11/2005 | Ghoshal | C08G 59/22 427/387 |
| 8,013,039 B2 | 9/2011 | Hsu et al. | |
| 8,133,957 B2 | 3/2012 | Hamamoto et al. | |
| 8,262,391 B2* | 9/2012 | Frances | A61K 6/0052 433/228.1 |
| 8,440,774 B2 | 5/2013 | Lin et al. | |
| 8,710,158 B2 | 4/2014 | Ueno et al. | |
| 8,822,593 B2 | 9/2014 | Onai et al. | |
| 9,045,641 B2 | 6/2015 | Yoshitake et al. | |
| 2005/0123776 A1 | 6/2005 | Yoshikawa | |
| 2006/0178444 A1 | 8/2006 | Frances | |
| 2008/0124822 A1 | 5/2008 | Yoshikawa | |
| 2009/0091045 A1 | 4/2009 | Tanikawa et al. | |
| 2010/0164127 A1 | 7/2010 | Noro | |

FOREIGN PATENT DOCUMENTS

TW 201350524 A 12/2013
TW 201527434 A 7/2015

OTHER PUBLICATIONS

Dworak et al., "Synthesis of Cycloaliphatic Substituted Silane Monomers and Polysiloxanes for Photocuring," Macromolecules, vol. 37, No. 25, 2004, pp. 9402-9417.
Huang, et al., "Studies on UV-Stable Silicone-Epoxy Resins," Journal of Applied Polymer Science, vol. 104, 2007, pp. 3954-3959.
Jang et al., "Synthesis and Cationic Photopolymerization of Epoxy-Functional Siloxane Monomers and Oligomers," Journal of Polymer Science: Part A: Polymer Chemistry, vol. 41, 2003, pp. 2056-3073.
Morita et al., "Cationic Copolymerization of Epoxy Siloxane Monomer with Liquid Poly-Butadiene and its Light Emitting Diode Encapsulation," Journal of Applied Polymer Science, vol. 109, 2008 (Published online Apr. 28, 2008), pp. 1808-1813.
Taiwanese Office Action and Search Report for Taiwanese Application No. 104142226, dated Jun. 16, 2016.

* cited by examiner

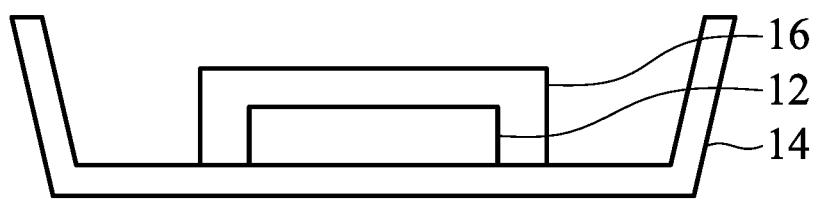

US 9,540,488 B1

SILOXANE RESIN COMPOSITION, AND PHOTOELECTRIC DEVICE EMPLOYING THE SAME

TECHNICAL FIELD

The disclosure relates to a siloxane resin composition and an optoelectronic device employing the same, and more particularly to a modified siloxane resin composition and an optoelectronic device employing the same.

BACKGROUND

Organic resin has high processability and is lightweight, low-cost, and impact resistant. Due to these properties, organic resin has gradually replaced inorganic compounds for use as a packaging material for light emitting diodes. Recently, due to the development of light-emitting diode techniques, there have been calls for organic siloxane resins and a packaging material with a high gas-barrier capability and good adhesion.

However, the conventional packaging material for a light emitting diode (such as siloxane resin) has insufficient gas-barrier capability and adhesion. Therefore, a novel siloxane resin with a high gas-barrier capability and good adhesion is required to solve the aforementioned problems.

SUMMARY

According to embodiments of the disclosure, the disclosure provides a siloxane resin composition, such as a siloxane resin composition including a modified siloxane. The siloxane resin composition includes (a) 45-87 parts by weight of a first siloxane compound, the first siloxane compound has a structure represented by Formula (I)

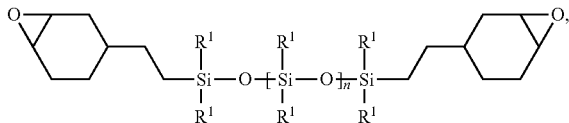

Formula (I)

wherein each $R^1$ is independently $C_{1-3}$ alkyl group, and n is an integer from 2 to 15; (b) 5-35 parts by weight of a second siloxane compound represented by Formula (II)

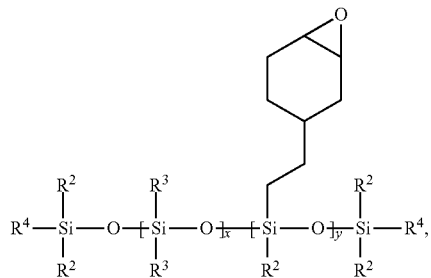

Formula (II)

wherein each $R^2$ and $R^3$ are independently $C_{1-3}$ alkyl group; each $R^4$ is independently $C_{1-3}$ alkyl group, or epoxy group; x≥1, y≥2, and x/y is from about 0.1 to 3; and (c) 2-20 parts by weight of a third siloxane compound represented by Formula (III)

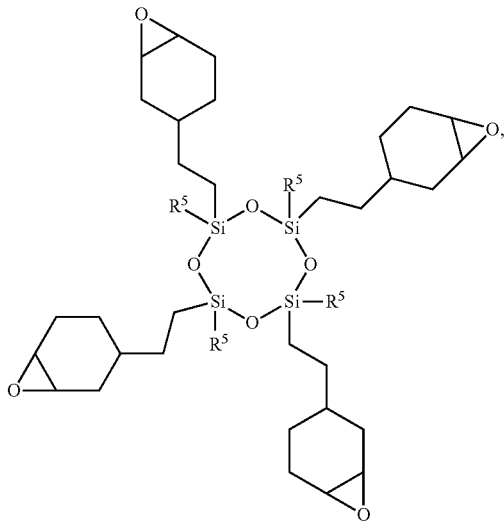

Formula (III)

wherein each R5 is independently $C_{1-3}$ alkyl group, wherein the sum of the first siloxane compound, the second siloxane compound, and the third siloxane compound is 100 parts by weight.

According to other embodiments of the disclosure, the disclosure also provides an optoelectronic device. The optoelectronic device includes an optoelectronic element; and a siloxane resin material layer disposed on the optoelectronic element, wherein the siloxane resin material layer is made from the aforementioned siloxane resin composition.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 is a schematic view of an optoelectronic device according to an embodiment of the disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

The disclosure provides a siloxane resin composition, and an optoelectronic device employing the same. According to an embodiment of the disclosure, the siloxane resin composition of the disclosure is prepared from three different functional siloxane compounds (including the terminal epoxy siloxane resin with specific chain length (i.e. the first siloxane compound), the side-chain epoxy siloxane resin with specific functional group ratio (i.e. the second siloxane compound), and the cyclic epoxy siloxane resin (i.e. the third siloxane compound), wherein there is a specific weight ratio between the three different functional siloxane compounds. As a result, the cured product of the siloxane resin composition of the disclosure (i.e. siloxane resin material) exhibits high light-thermal stability, low stress, and high gas-barrier properties, and is suitable for use as a packaging material in the packaging structure of various optoelectronic devices.

According to an embodiment of the disclosure, the siloxane resin composition includes (a) a first siloxane compound represented by Formula (I)

Formula (I)

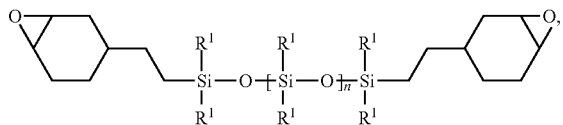

wherein each $R^1$ is independently $C_{1-3}$ alkyl group, and n is an integer from 2 to 15; (b) a second siloxane compound represented by Formula (II)

Formula (II)

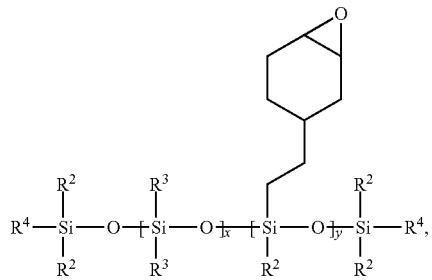

wherein each $R^2$ and $R^3$ are independently $C_{1-3}$ alkyl group; each $R^4$ is independently $C_{1-3}$ alkyl group, or epoxy group; $x \geq 1$, $y \geq 2$, and x/y is from about 0.1 to 3. When x/y is less than about 0.1, the siloxane resin material exhibits high stress and low tenacity due to the extremely high cross-linking density. When x/y is greater than about 3, the siloxane resin material exhibits inferior gas-barrier properties and adhesion due to the extremely low cross-linking density. The siloxane resin composition includes (c) a third siloxane compound represented by Formula (III)

Formula (III)

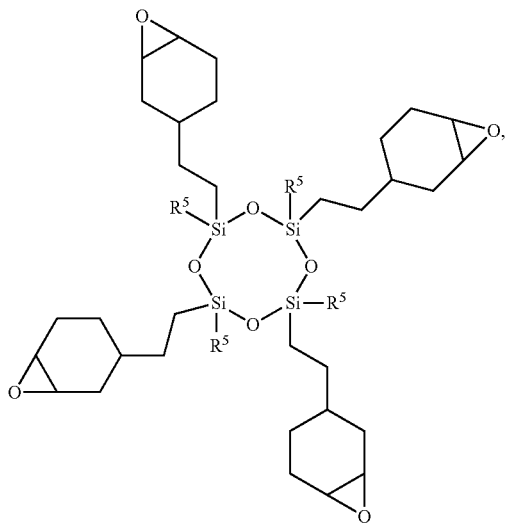

wherein each $R^5$ is independently $C_{1-3}$ alkyl group. For example, the first siloxane compound can have a molecular weight (such as weight average molecular weight) from about 500 to 1500. The second siloxane compound can have a molecular weight (such as weight average molecular weight) from about 2800 to 5300. The third siloxane compound can have a molecular weight (such as weight average molecular weight) from about 700 to 900.

According to some embodiments of the disclosure, the first siloxane compound (terminal epoxy siloxane resin) is present in the amount of about 45-87 parts by weight for reducing the stress on the siloxane resin composition, wherein the sum of the first siloxane compound, the second siloxane compound, and the third siloxane compound is 100 parts by weight. When the amount of first siloxane compound in the siloxane resin composition is too low, the siloxane resin composition exhibits larger stress and poor light-thermal stability. On the other hand, when the amount of first siloxane compound in the siloxane resin composition is too high, the siloxane resin composition exhibits inferior gas-barrier properties.

According to some embodiments of the disclosure, the addition of the second siloxane compound (side-chain epoxy siloxane resin) and third siloxane compound (cyclic epoxy siloxane resin) can increase the cross-linking density of the siloxane resin composition, resulting in the cured product of the siloxane resin composition (i.e. siloxane resin material) having a net structure with high cross-linking density and exhibiting improved adhesion.

The second siloxane compound can be present in the amount of about 5-35 parts by weight, and the third siloxane compound can be present in the amount of about 2-20 parts by weight. When the amount of second siloxane compound and third siloxane compound in the siloxane resin composition is too low, the cured product of the siloxane resin composition (i.e. siloxane resin material) exhibits poor gas-barrier properties due to the insufficient cross-linking density. On the other hand, when the amount of second siloxane compound and third siloxane compound in the siloxane resin composition is too high, the cured product of the siloxane resin composition exhibits high stress due to the extremely high cross-linking density.

According to other embodiments of the disclosure, the siloxane resin composition can further include: (d) 20-50 parts by weight of a curing agent. For example, the curing agent can be an anhydride curing agent. As a result, besides high light-thermal stability, low stress, and high gas-barrier properties, the cured product of the siloxane resin composition exhibits high visible light transmittance (larger than 90%). The anhydride curing agent can be methyl hexahydrophthalic anhydride, methyl tetrahydrophthalic anhydride, maleic anhydride (HA), polystyrene-co-maleic anhydride (SMA), or a combination thereof, but the disclosure is not limited thereto.

In addition, according to some embodiments of the disclosure, the curing agent can also be an aliphatic amine curing agent, cyclic aliphatic amine curing agent, aromatic-aliphatic amine curing agent, phenolic curing agent, or a combination thereof. For example, the aliphatic amine curing agent can be JEFFAMINE® D-230 polyetheramine. The cyclic aliphatic amine curing agent can be diaminocyclohexane. The aromatic-aliphatic amine curing agent can be oxydianiline, or stearyl amine ethoxylate (SAA). The phenolic curing agent can be phenol-formaldehyde novolac (such as HRJ series), or melamine phenol novolac. The curing agents described above are only exemplary. The aliphatic amine curing agent, cyclic aliphatic amine curing agent, aromatic-aliphatic amine curing agent, and the phenolic curing agent of the disclosure are not limited thereto.

According to embodiments of the disclosure, in order to promote the cross-linking reaction rate, the siloxane resin composition can further include (e) 0.1-1 parts by weight of a reaction accelerator, wherein the reaction accelerator can be quaternary phosphate, amine, or a combination thereof.

In addition, the siloxane resin composition of the disclosure can further include (f) 0.1-5 parts by weight of an additive, wherein the additive can include a reaction accelerator, an adhesion promoter, antioxidant, defoamer, leveling agent, stabilizer, or a combination thereof.

According to an embodiment of the disclosure, in order to achieve elimination of volatiles or small molecule compounds during packaging process and maintain the yield and reliability of products, the siloxane resin composition of the disclosure does not include any solvent (such as organic solvent or water).

According to an embodiment of the disclosure, the siloxane resin composition of the disclosure can be coated on a substrate or an optoelectronic element, and subjected to a curing process, thereby obtaining an optoelectronic device. The optoelectronic element can be light-emitting diode, laser diode, or optical receiver.

For example, as show in FIG. 1, the optoelectronic device 10 of the disclosure can include an optoelectronic element 12 disposed on a reflective cup 14, and a siloxane resin material layer 16 disposed on the optoelectronic element 12, wherein the siloxane resin material layer 16 is made from the siloxane resin composition of the disclosure. A packaging layer made from the siloxane resin composition of the disclosure can exhibit improved light and thermal stability and reduced stress in comparison with the conventional epoxy resin packaging material, and exhibit better gas-barrier properties and lower gas permeability in comparison with the conventional siloxane resin.

Below, exemplary embodiments will be described in detail so as to be easily realized by a person having ordinary knowledge in the art.

Preparation of Siloxane Compound

Preparation Example 1

37.2 g of 4-vinyl-1-cyclohexene-1,2-epoxide, 5 ppm of tris(dibutylsulfide)rhodium trichloride, and 100 ml of toluene were added into a reaction bottle, and then the reaction bottle was heated to 100° C. Next, 100 g of hydrogen-containing polysiloxane compound (sold by Gelest, Inc. with a trade No. of DMS-H03) was slowly added into the reaction bottle at 100° C. After the addition of DMS-H03 was complete, the reaction bottle was heated and stirred at 115° C. FT-IR analysis indicated the reaction was complete, as judged by the absence of a SiH band (2160 cm$^{-1}$) in the FT-IR spectrum. After the reaction was complete, the reaction bottle was cooled to room temperature. Next, the charcoal was added into the reaction bottle for purification. Finally, after removing the charcoal by filtration and removing the toluene by rotary evaporation, Siloxane Compound (1) represented by

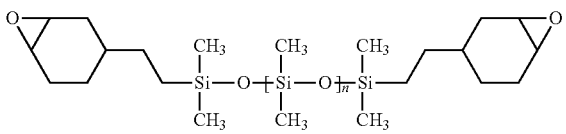

was obtained, wherein the average value of n was about 4.5 and the average epoxide equivalent weight (EEW) of Siloxane Compound (1) was about 475.

Siloxane Compound (1) was analyzed by nuclear magnetic resonance (NMR) spectroscopy and the result is as follows: $^1$H NMR: 0.04 ppm (s, CH$_3$—Si), 0.48 ppm (m, 0.17-2.18 ppm (m, cyclohexyl group), 3.12 ppm (m, epoxy group).

Preparation Example 2

9.93 g of 4-vinyl-1-cyclohexene-1,2-epoxide, 10 ppm of tris(dibutylsulfide)rhodium trichloride, 0.0015 g of N,N-dioctadecylmethylamine, and 50 ml of toluene were added into a reaction bottle, and then the reaction bottle was heated to 100° C. Next, 19.5 g of copolymer of methyl siloxane and dimethyl silane (sold by Gelest, Inc. with a trade No. of HMS-301) was added into the reaction bottle at 100° C. After the addition of HMS-301 was complete, the reaction bottle was heated and stirred at 115° C. until the reaction was complete. Next, the reaction bottle was cooled to room temperature. Next, the charcoal was added into the reaction bottle for purification. Finally, after removing the charcoal by filtration and removing the toluene by rotary evaporation, Siloxane Compound (2) represented by

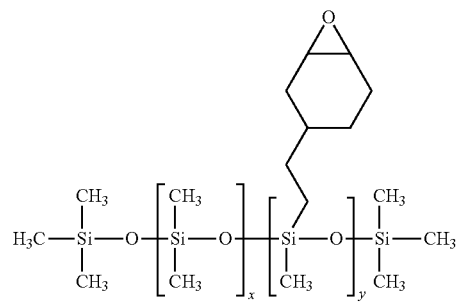

was obtained, wherein x was larger than 1, y was larger than or equal to 2, and x/y was from about 0.33 to 0.54. The weight average molecular weight of Siloxane Compound (2) was from about 2800 to 3200, and the average epoxide equivalent weight (EEW) of Siloxane Compound (2) was 370.

Preparation Example 3

59.52 g of 4-vinyl-1-cyclohexene-1,2-epoxide, 100 ppm of tris(dibutylsulfide)rhodium trichloride, 0.0015 g of N,N-dioctadecylmethylamine, and 50 m of ltoluene were added into a reaction bottle, and then the reaction bottle was heated to 100° C. Next, 24 g of 1,3,5,7-tetramethylcyclotetrasiloxane (sold by Gelest, Inc.) was dropwisely added into the reaction bottle at 100° C. After the addition of 1,3,5,7-tetramethylcyclotetrasiloxane was complete, the reaction bottle was heated and stirred at 115° C. until the reaction was complete. Next, the reaction bottle was cooled to room temperature. Next, the charcoal was added into the reaction bottle for purification. Finally, after removing the charcoal by filtration and removing the toluene by rotary evaporation, Siloxane Compound (3) represented by

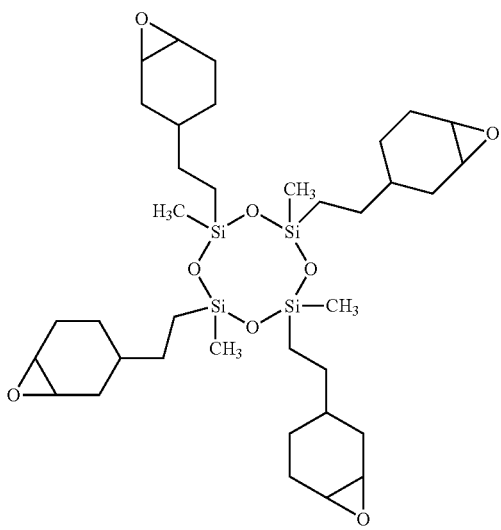 [SMILES: C[Si]1(CCC2CCC3OC3C2)O[Si](C)(CCC2CCC3OC3C2)O[Si](C)(CCC2CCC3OC3C2)O[Si](C)(CCC2CCC3OC3C2)O1]

was obtained. The average epoxide equivalent weight (EEW) of Siloxane Compound (3) was about 184.

Preparation of Siloxane Resin Composition
(Hereinafter "Packaging Composition")

Example 1

First, 28.98 g of methyl hexahydrophthalic anhydride (MHHPA) serving as a curing agent, 0.21 g of amine reaction accelerator (sold by San-Apro Ltd. With a trade No. of U-Cat 18X), and 0.83 g of organic phosphite and hindered phenolic antioxidant compound (sold by Double Bond Chemical Ind. Co., Ltd with a trade No. of TP-10H) were added into a reaction bottle and mixed by planetary mixer at a speed of 2000 rpm for 5 minutes. After defoaming at a speed of 2200 rpm for 5 minutes, a mixture was obtained. Next, 40.89 g of Siloxane Compound (1), 21.87 g of Siloxane Compound (2), 6.54 g of Siloxane Compound (3), and 0.69 g of the adhesion promoter represented by

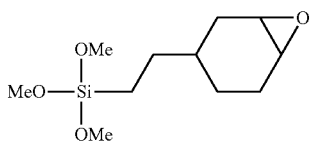 [SMILES: CO[Si](CCC1CCC2OC2C1)(OC)OC]

(sold by Shin-Etsu Chemical Co., Ltd. with a trade No. of KBM-303) were added into the planetary mixer and mixed with the mixture at a speed of 2000 rpm for 10 minutes. Next, the result was defoamed by the planetary mixer at a speed of 2200 rpm for 10 minutes, obtaining Packaging Composition (1). The components and amounts of Packaging Composition (1) was shown in Table 1.

Examples 2-5

Examples 2-5 were performed in the same manner as in Example 1 except that the amounts of the MHHPA, U-Cat 18X, TP-10H, Siloxane Compound (1), Siloxane Compound (2), Siloxane Compound (3), and KBM-303 were allocated according to Table 1, obtaining Packaging Compositions (2)-(5).

TABLE 1

|  | Example 1 | Example 2 | Example 3 | Example 4 | Example 5 |
| --- | --- | --- | --- | --- | --- |
| Siloxane Compound (1) | 40.89 g | 47.83 g | 54.45 g | 60.76 g | 57.63 g |
| Siloxane Compound (2) | 21.87 g | 17.30 g | 12.48 g | 8.12 g | 13.21 g |
| Siloxane Compound (3) | 6.54 g | 5.10 g | 3.73 g | 2.43 g | 3.95 g |
| KBM-303 | 0.69 g | 0.70 g | 0.71 g | 0.71 g | 0.75 g |
| MHHPA | 28.98 g | 28.25 g | 27.56 g | 27.56 g | 23.34 g |
| U-Cat 18X | 0.21 g | 0.21 g | 0.21 g | 0.21 g | 0.22 g |
| TP-10H | 0.83 g | 0.84 g | 0.85 g | 0.85 g | 0.90 g |

Comparative Examples 1-5

Comparative Examples 1-5 were performed in the same manner as in Example 1 except that the amounts of the MHHPA, U-Cat 18X, TP-10H, Siloxane Compound (1), Siloxane Compound (2), Siloxane Compound (3), and KBM-303 were allocated according to Table 2, obtaining Packaging Compositions (6)-(10).

TABLE 2

|  | Comparative Example 1 | Comparative Example 2 | Comparative Example 3 | Comparative Example 4 | Comparative Example 5 |
| --- | --- | --- | --- | --- | --- |
| Siloxane Compound (1) | 17.71 g | 72.50 g | 52.00 g | 0 g | 58.57 g |
| Siloxane Compound (2) | 37.88 g | 0 g | 19.86 g | 55.85 g | 0 g |
| Siloxane Compound (3) | 11.33 g | 0 g | 0 g | 10.74 g | 10.04 g |
| KBM-303 | 0.67 g | 0.72 g | 0.72 g | 0.67 g | 0.69 g |
| MHHPA | 31.38 g | 25.68 g | 26.32 g | 31.72 g | 29.65 g |
| U-Cat 18X | 0.20 g | 0.22 g | 0.22 g | 0.20 g | 0.21 g |
| TP-10H | 0.80 g | 0.81 g | 0.86 g | 0.80 g | 0.82 g |

Properties Measurement of the Cured Product Prepared from Packaging Composition

Packaging Compositions (1)-(10) of Examples 1-5 and Comparative Examples 1-5 were added into dispensing syringes individually, and then defoamed in a vacuum oven for 30-60 minutes. Next, Packaging Compositions (1)-(10) were used for packaging light-emitting diodes (e.g. PLCC 5050 LED). After coating, Packaging Compositions (1)-(10) were baked at 130° C. for 1 hour, and baked at 160° C. for 2 hour, obtaining light-emitting devices with Cured layers (1)-(10) respectively. Next, the Cured layers (1)-(10) were subjected to a light transmittance test (at a wavelength of 450 nm), thermal cycle test (conducted by carrying out 300 cycles of cooling at −40° C. for 15 minutes, heating from −40 up to 120° C. within less than 1 minute, and heating at 120° C. for 15 minutes), and gas-barrier test (disposing the light-emitting diodes in a saturated sulfur vapor atmosphere and determining if the silver plated frame of the light-emitting diode was blackened). The results were shown in Table 3.

TABLE 3

| | light transmittance (%) | thermal cycle test (number of passed samples/number of samples) | surfurization test (the silver plated frame was blackened or not) |
|---|---|---|---|
| Cured layer (1) | 91% | 22/22 | not blackened after 48 hours |
| Cured layer (2) | 92% | 22/22 | not blackened after 48 hours |
| Cured layer (3) | 92% | 22/22 | not blackened after 48 hours |
| Cured layer (4) | 93% | 22/22 | not blackened after 48 hours |
| Cured layer (5) | 92% | 22/22 | not blackened after 48 hours |
| Cured layer (6) | 91% | 0/22 | not blackened after 48 hours |
| Cured layer (7) | 94% | 22/22 | blackened at about 4 hours |
| Cured layer (8) | 92% | 13/22 | blackened at about 16 hours |
| Cured layer (9) | 91% | 0/22 | not blackened after 48 hours |
| Cured layer (10) | 92% | 16/22 | blackened at about 10 hours |

As shown in Table 1-3, in comparison with the compositions of Examples 1-5, Cured layers (7-8 and 10) prepared by the compositions of Comparative Examples 2-3 and 5 exhibits inferior gas-barrier properties (blackened within 16 hours after being disposed in the saturated sulfur vapor atmosphere) due to the absence of Siloxane Compound (2) and/or Siloxane Compound (3). Furthermore, when the amount of Siloxane Compound (1) of the composition is too low or the composition does not have Siloxane Compound (1), the cured layer of the composition exhibits high stress, and low light-thermal stability, resulting in the light-emitting diode employing the same not being able to pass the thermal cycle test.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A siloxane resin composition, comprising:

(a) 45-87 parts by weight of a first siloxane compound represented by Formula (I)

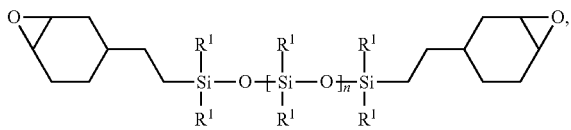

Formula (I)

wherein each $R^1$ is independently $C_{1-3}$ alkyl group, and n is an integer from 2 to 15;

(b) 5-35 parts by weight of a second siloxane compound represented by Formula (II)

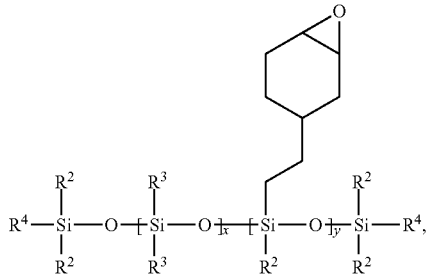

Formula (II)

wherein each $R^2$ and $R^3$ are independently $C_{1-3}$ alkyl group; each $R^4$ is independently $C_{1-3}$ alkyl group, or epoxy group; x≥1, y≥2, and x/y is from 0.1 to 3; and (c) 2-20 parts by weight of a third siloxane compound represented by Formula (III)

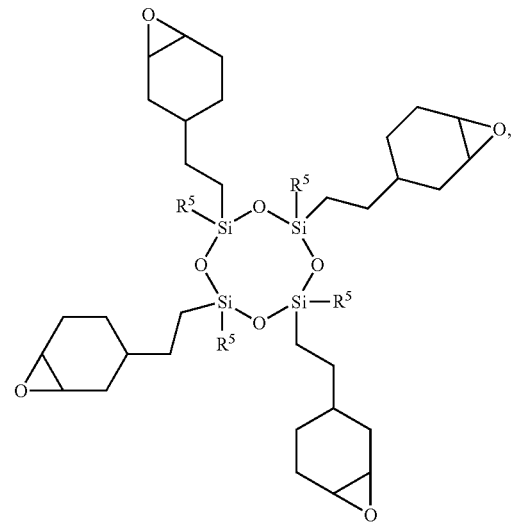

Formula (III)

wherein each $R^5$ is independently $C_{1-3}$ alkyl group, wherein the sum of the first siloxane compound, the second siloxane compound, and the third siloxane compound is 100 parts by weight.

2. The siloxane resin composition as claimed in claim 1, further comprising:

(d) 20-50 parts by weight of a curing agent.

3. The siloxane resin composition as claimed in claim 2, wherein the curing agent is an anhydride curing agent.

4. The siloxane resin composition as claimed in claim 3, wherein a cured product of the siloxane resin composition has a visible light transmittance greater than 90%.

5. The siloxane resin composition as claimed in claim 2, wherein the curing agent is aliphatic amine curing agent, cyclic aliphatic amine curing agent, aromatic-aliphatic amine curing agent, phenolic curing agent, or a combination thereof.

6. The siloxane resin composition as claimed in claim 1, further comprising:

(e) 0.1-1 parts by weight of a reaction accelerator.

7. The siloxane resin composition as claimed in claim 6, wherein the reaction accelerator comprises quaternary phosphate, amine, or a combination thereof.

8. The siloxane resin composition as claimed in claim 1, further comprising:

(f) 0.1-5 parts by weight of an additive.

9. The siloxane resin composition as claimed in claim 8, wherein the additive comprise a reaction accelerator, an adhesion promoter, antioxidant, defoamer, leveling agent, stabilizer, or a combination thereof.

10. An optoelectronic device, comprising:

an optoelectronic element; and a siloxane resin material layer disposed on the optoelectronic element, wherein the siloxane resin material layer is made from the siloxane resin composition as claimed in claim 1.

11. The optoelectronic device as claimed in claim 10, wherein the optoelectronic element comprises a light-emitting diode, laser diode, or optical receiver.

\* \* \* \* \*